United States Patent [19]
Thompson et al.

[11] Patent Number: 4,710,166
[45] Date of Patent: Dec. 1, 1987

[54] AUTOMATED DRUG ADDITIVE INFUSION SYSTEM

[75] Inventors: Thomas C. Thompson, McKinney; David J. Harrison, Carrollton, both of Tex.

[73] Assignee: Quest Medical, Inc., Carrollton, Tex.

[21] Appl. No.: 796,108

[22] Filed: Nov. 8, 1985

[51] Int. Cl.⁴ ............................................. A61M 5/14
[52] U.S. Cl. ........................................ 604/81; 604/65; 604/123
[58] Field of Search ..................... 604/81, 65–67, 604/245, 151, 152, 153, 123

[56] References Cited
U.S. PATENT DOCUMENTS

| | | | |
|---|---|---|---|
| 3,985,133 | 10/1976 | Jenkins | 604/67 |
| 4,213,454 | 7/1980 | Shim | 604/123 |
| 4,265,240 | 5/1981 | Jenkins | 604/81 |
| 4,276,004 | 6/1981 | Hahn | 604/153 |
| 4,303,376 | 12/1981 | Siekmann | 604/153 |
| 4,369,780 | 1/1983 | Sakai | 604/123 |
| 4,391,598 | 7/1983 | Thompson | 604/81 |
| 4,410,322 | 10/1983 | Archibald | 604/153 |
| 4,453,931 | 6/1984 | Pastrone | 604/123 |
| 4,553,958 | 11/1985 | LeCocq | 604/81 |

Primary Examiner—C. Fred Rosenbaum
Assistant Examiner—Gene B. Kartchner
Attorney, Agent, or Firm—Roger C. Clapp

[57] ABSTRACT

This invention relates to the parenteral infusion of fluids into patients, and particularly to the addition of drugs or other secondary fluids in infusion systems operating on an automatic basis.

6 Claims, 11 Drawing Figures

AUTOMATED DRUG ADDITIVE INFUSION SYSTEM

BACKGROND ART

Parenteral drug administration systems have been used in patient care for many years, typically operated by gravity or by mechanical pump mechanisms.

Quite often it has proven desirable to introduce more than one fluid to the patient in administration systems operated under the control of electronic instrumentation either on a gravity delivery or a positive pressure basis. While two or more separate blood vessel entries may be made, each entry involves trauma to the patient, lost nursing time, and the potential risk of infection or other harmful results. Therefore, it has been recognized as desirable to employ a drug additive system in which a primary fluid is introduced, and a secondary fluid may be introduced intermittently through the same entry ("piggybacking"). The primary fluid may function for fluid replacement, electrolytic balance, nutrition, keeping vein open (KVO), blood administration, or drugs. The secondary fluid to be administered may be an antibiotic, anticoagulant, antihypertensive, cardiovascular agent or other medicament.

One prior art system for automatically administering two separate fluids sequentially under electronic control is disclosed in U.S. Pat. No. 4,391,598. In that system, an electronic infusion control device operates on a tubing set carrying the parenteral fluid. A Y-connector is located upstream of the device and is supplied by two fluid lines from two separate fluid containers. A one-way check valve is positioned in the line between the Y-connector and the primary fluid container. The secondary fluid container is hung higher than the primary container so that the gravitational head of the secondary fluid closes the check valve to prevent flow into or from the primary container. With this setup, the secondary fluid will be delivered to the patient and, when the secondary fluid head has been diminished, the check valve will open automatically to commence delivery of the primary fluid. The infusion control device may automatically be set up at two different delivery rates for the primary and secondary fluid delivery. When the volume to be delivered at the secondary fluid rate has been delivered, the instrument automatically converts to the selected primary fluid administration rate. This system has proven to be very advantageous for delivery instrumentation which does not positively draw the fluid from the supply container, permitting the check valve to ensure the sole delivery of the secondary fluid without dilution by the primary fluid. It does not, however, permit sequential delivery by mechanisms which would pull both fluids from the container. Moreover, the check valve required to implement the system makes the administration set more expensive. In view of the importance of minimizing the costs of medical care delivery, this may be significant since the administration set must be replaced every day or two. It also requires that the user suspend the primary container below the level of the secondary container.

Another approach to adapting electronic instrumentation is reflected in the IMED 380 controller manufactured by IMED Corporation of San Diego, Calif. This instrument does not control flow volumentrically, but to a selected rate of drops falling in a drip chamber situated in the fluid line below the supply container. This drop rate is sensed by a photoelectric sensor removably secured to the drip chamber. Provision is made for drug additives by joining two lines in a Y-connector at the instrument, and providing a valve on the instrument through which the secondary line passes, and a check valve on the primary line. The instrument may thus maintain the primary line in check as long as secondary fluid flows. When a secondary drug container is being used, an additional drop sensor is used on the drip chamber of the secondary container. When the drop sensors indicate that drops are falling from the secondary container, the instrument permits flow through the secondary line. When the drop sensor of the secondary drip chamber indicates the cessation of drop fall, the secondary valve closes the secondary line, and the drop rate is thereafter controlled at the drop rate selected by the user for the primary fluid. From the standpoint of volumetric control, this instrument has the disadvantage of relying simply upon a rate of drop fall, and drops may be quite variable in volumetric size. This variance is produced by variations in fluid type, fluid temperature, driving pressure head, selected flow rate, as well as in variations in the orifice for forming the drop in the drip chamber. Moreover, the closure of the secondary line as soon as drops cease falling into the drip chamber results in wastage of the drug to the extent of the fluid contained in the drip chamber and in the line downstream to the Y-connector. This wastage of drug may be particularly significant when the drugs are packaged in relatively small containers. The system also requires two drop sensors, and correct placement of the sensors on the correct drip chambers.

Yet another approach to automated control of the sequential delivery of two fluids using electronic infusion devices is reflected in the IVAC 460 unit manufactured by IVAC Corporation of San Diego, Calif. A shutoff valve is provided for each of two lines extending from the secondary and primary fluid containers into the device. When a secondary fluid is to be delivered, the user may enter a volumetric amount representing the quantity of drug to be delivered and a specific flow rate for that drug, along with a flow rate to which the system will revert on completion of secondary delivery. A major difficulty with this system is that the user cannot know with certainty the volumetric contents of the supply container. If the selected volume entered is too high in comparison to the actual contents of the bag, the result will be an empty container alarm by the instrument rather than an automatic switchover to the administration of the primary fluid. If the volume entered is too little, all of the drug provided by the pharmacy will not be delivered.

The control system contemplated by this invention overcomes the disadvantages of these various approaches to the vexing problem of providing an effective and economical system for administration of two fluids sequentially through a common entry site.

SUMMARY OF THE INVENTION

In accordance with this invention, there is provided a system for sequentially administering to a patient fluids from a secondary fluid container and a primary fluid container at respective selected flow rates governed at a rate control site by an electromechanical device. The system includes a Y-connector upstream from the control site, a primary fluid line extending from the primary fluid container through a primary valve to the Y-connector and a secondary fluid line extending from the secondary fluid container to the Y-connector through a secondary valve. An output flow line extends from the Y-connector through the control site. The invention includes detection means for automatically detecting the absence of fluid in the secondary line immediately adjacent the Y-connector, and means operative to close the secondary valve and open the primary valve, in response to such detection by the detection means.

In a specific embodiment of the invention wherein the control site includes a cassette filled from the supply containers by gravity, the Y-connector is secured no higher than the approximate height of the cassette, and the detection means comprises means for detecting the lack of fluid filling the cassette.

In another form of the invention, the detection means comprises an air-in-line detector used with the secondary line above the Y-connector. In this form, it is not necessary to position the Y-connector at or below the height of the cassette.

BRIEF DESCRIPTION OF THE DRAWINGS

A more complete understanding of the invention can be had by referring to the following Detailed Description together with the accompanying Drawings, wherein:

FIGS. 2–11 illustrate an electronic infusion control device, a pump, and disposable cassette to which this invention is preferably applied;

Specifically.

DETAILED DESCRIPTION

Figure 1:
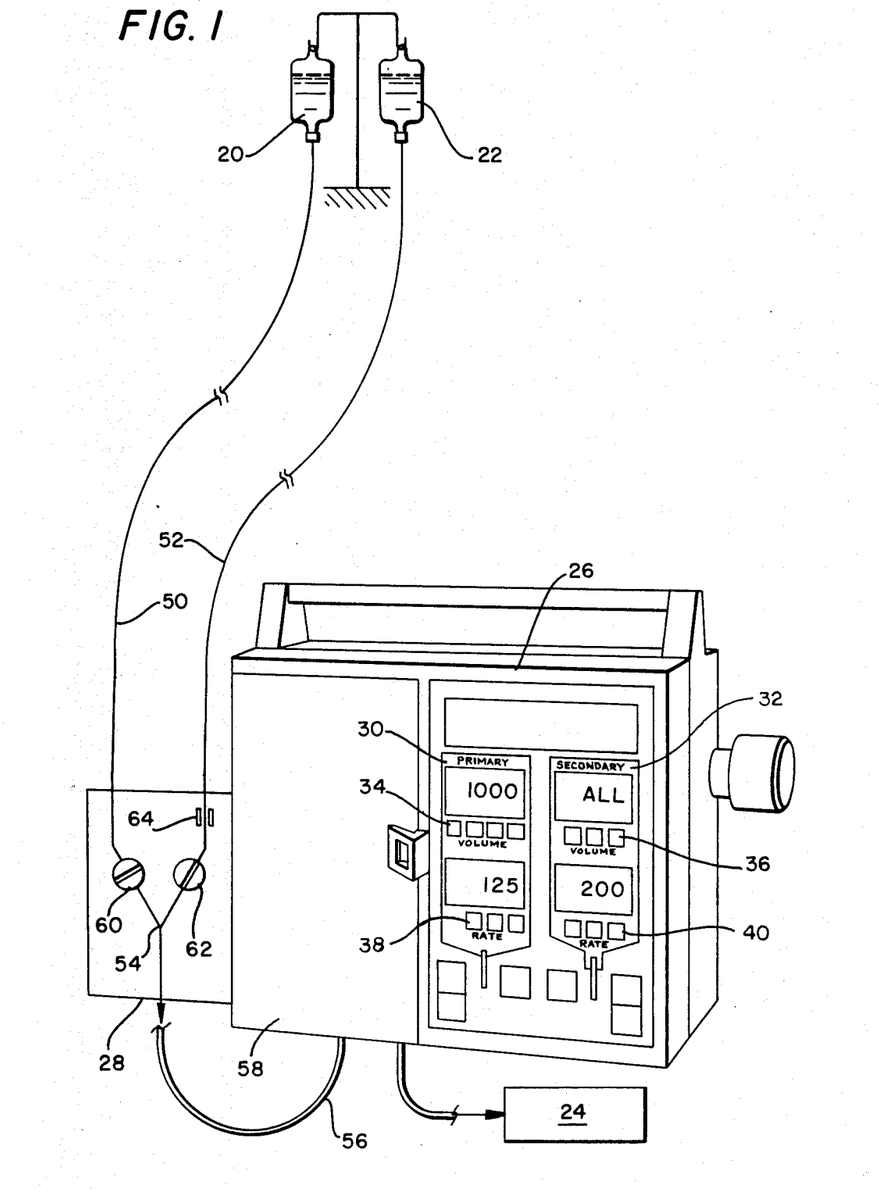
FIG. 1 schematically illustrates a system assembled in accordance with the present invention for sequential delivery of two fluids.

In FIG. 1, there is illustrated a system for sequentially delivering two fluids, contained in a primary fluid container 20 and a secondary fluid container 22, to a patient 24. The system employs a pump or intravenous fluid controller 26 in combination with an additive module 28. The electronic infusion device 26 may employ any of a variety of infusion mechanisms known for providing controlled patient infusion at a rate control site. Preferably, it is a variable pressure pumping device of the type disclosed in co-pending patent application Ser. No. 717,131, now U.S. Pat. No. 4,657,490, entitled "Infusion Pump with Disposable Cassette", and assigned to the owner of this application, which is incorporated herein by reference. Device 26 has an input/display panel provided with input/display means 30 pertaining to the primary fluid and input/display means 32 pertaining to the secondary fluid. Each of the displays 30 and 32 are provided respectively with fluid volume to be delivered displays and input pads 34 and 36, respectively. The pads provide for operator setting of the volumes to be delivered of each type. On the secondary volume to be delivered display and input pads 36, the user may, as illustrated in the drawing, by increasing the numerical volume setting above the highest number available (999 in the illustration), set the secondary volume for "all".

Each of the displays 30 and 32 also include rate display and input pads 38 and 40 respectively, for selection and display of an infusion rate for each fluid.

A primary fluid line 50 extends toward the device 26 from primary fluid container 20. Similarly, a secondary fluid line 52 extends from the secondary fluid container 22 toward the device 26. Lines 50 and 52 are joined at Y-connector 54. Output line 56 leads away from connector 54 toward the rate control site provided behind door 58 of the infusion control device 26. Additive module 28 receives the Y-connector 54 and the three lines extending from the connector, 50, 52 and 56. Module 28 is preferably mounted adjacent the device 26. Primary line 50 is extended through a primary fluid valve 60, indicated schematically, positioned on module 28. Likewise, secondary line 52 extends through secondary valve 62 situated on additive module 28. Valves 60 and 62 may be of any type, including pinching members capable of closing off their respective lines. In addition, secondary line 52 is threaded between two sides of a conventional air-in-line detector 64 for the detection of air, located immediately upstream from valve 62 and connector 54.

When the additive feature is not in use, it is not necessary to utilize the additive module 28. In this mode of operation, control device 26 may be set up with a volume and rate for the primary fluid to which the unit will then control.

If, however, a piggyback additive is to be employed, the device is assembled as schematically illustrated in FIG. 1. With an additive set in position on the additive module 28, control device 26 is set to control valves 60 and 62 in accordance with the instructions input in the primary and secondary displays 30 and 32. After inputting the desired volumes and rates through pads 34, 36, 38 and 40, the operator causes the instrument to activate, and the control device 26 initially causes primary valve 60 to close and secondary valve 62 to open.

Delivery of fluid will therefore be from the secondary fluid connector 22 through line 52 and line 56 through the control site to the patient. If the operator has chosen to enter "all" in the secondary volume to be delivered display, this delivery will continue until the air-in-line sensor 64 detects the presence of air adjacent the Y-connector 54. Upon such detection, the condition of valves 60 and 62 are reversed so that secondary valve 62 is closed and primary valve 60 is opened, and the control device 26 will begin forwarding fluid at the rate selected for the primary fluid. In the event that the operator has selected a numerical volumetric limit for secondary fluid infusion, the valve switch will occur when that limit is reached, provided air has not been sensed in the secondary line adjacent the connector by the air-in-line detector 52. If air were detector adjacent connector 54 prior to a numerical volume limit of secondary infusion being reached, the air-in-line detector 52 would govern and cause valve 62 to close. Either an alarm can be given at this point, or the primary valve 60 opened and infusion continued at the selected primary rate.

It is also possible to use an alternate means for detecting the lack of fluid in the secondary line adjacent connector 54 in the event of certain types of control devices 26 being used. If the device 26 is of the type disclosed in co-pending application Ser. No. 717,31, now U.S. Pat. No. 4,657,490, as described below in conjunction with FIGS. 2-11 depicting the pump and its disposable pump cassette, the device pumps fluid provided to the pump cassette by gravity flow, and then by pressurizing the fluid in a pump chamber to push it through the output line to the patient. In that type of device, where the pressure being created in the cassette is directly measured by the device 26, the air-in-line detector 64 may be dispensed with. In such event the Y-connector 54 should be located at a height no greater than the approximate height of the cassette.

Thus, the secondary fluid will cease to gravity fill the cassette when the top of the secondary fluid column is drawn down adjacent connector 54. This condition will be detected by the absence of pumping pressure. The lack of pressure will then be used as the equivalent of the air-in-line detection of element 64 to close secondary valve 62, open primary valve 60, and cause the instrument to revert to the infusion rate selected for the primary fluid.

The preferred form of pump and pump cassette to which this invention may be applied in this manner are illustrated in FIGS. 2-11.

Figure 2:
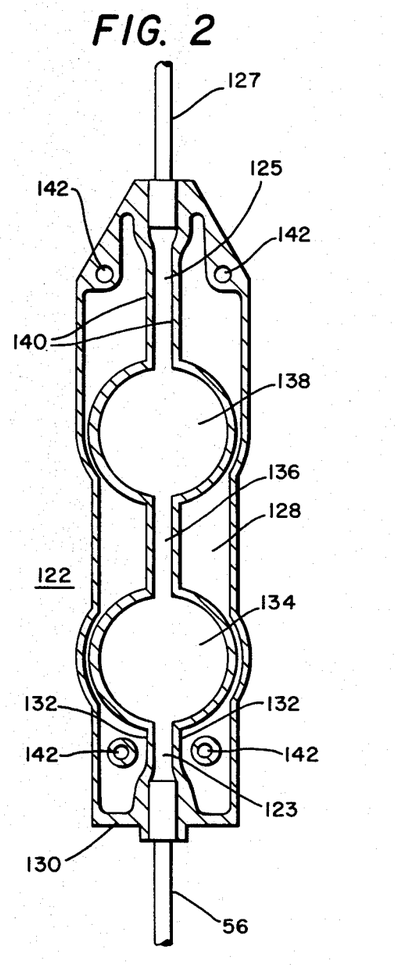
FIG. 2 is a front view of the disposable cassette.
Figure 3:
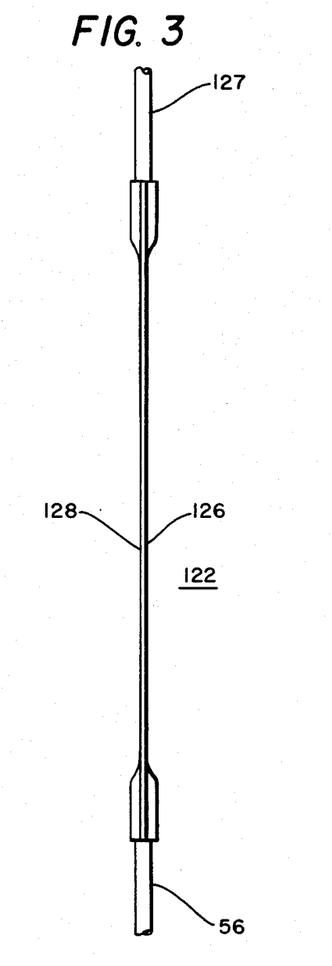
FIG. 3 is a side view of the disposable cassette.

Pump cassette 122, as best seen in FIGS. 2 and 3, is formed by a first flexible sheet 126 and a second flexible sheet 128, which may be formed from a suitable flexible sheet material, such as polyvinyl chloride. The cassette 122 may be assembled by bonding sheets 126 and 128 over a selected bonding area 130 indicated by hatching in FIG. 2. The bonding area 130 includes bonding along spaced parallel lines 132 in order to form a cassette inlet passage 123 extending from line 56 at one end of the cassette between sheets 126 and 128. Inlet passage 123 extends to a supply chamber 134 having a generally circular configuration. A transfer passage 136 extends from the side of supply chamber 134 opposite inlet passage 123, communicating with a pump chamber 138. Bonding along two parallel lines 140, extending from pump chamber 138, forms outlet passage 125.

Thus, there is provided longitudinally through the central area of cassette 122, a continuous fluid path extending from inlet 123 through supply chamber 134, transfer passage 136, and pump chamber 138 to the cassette outlet 125. Supply tube 56 is inserted into inlet passage 123 and bonded by any suitable means, such as by solvent bonding. Likewise, an outlet tube 127 is inserted into outlet passage 125 and bonded thereto. In the preferred form of the invention, the cassette is, as shown in FIG. 3, essentially flat. This permits production of the cassette from flat sheet without the necessity of any forming operation. Depending upon the material used for sheets 126 and 128, it may be desirable to provide slight relief by vacuum forming in one or both of the sheets along the open flow path formed by the cassette, in order to minimize adhesion of the unbonded areas during storage.

The flexibility of the cassette must be sufficient that, with fluid at a relatively low pressure being provided at the inlet 123, with the outlet 125 closed, fluid will flow into the cassette filling it and causing the chambers 134 and 138 to bulge with fluid by stretching of the sheets 126 and 128. Four mounting holes 142 are provided in the margins of the cassette for positioning and mounting of the cassette in the pump 26.

Figure 4:
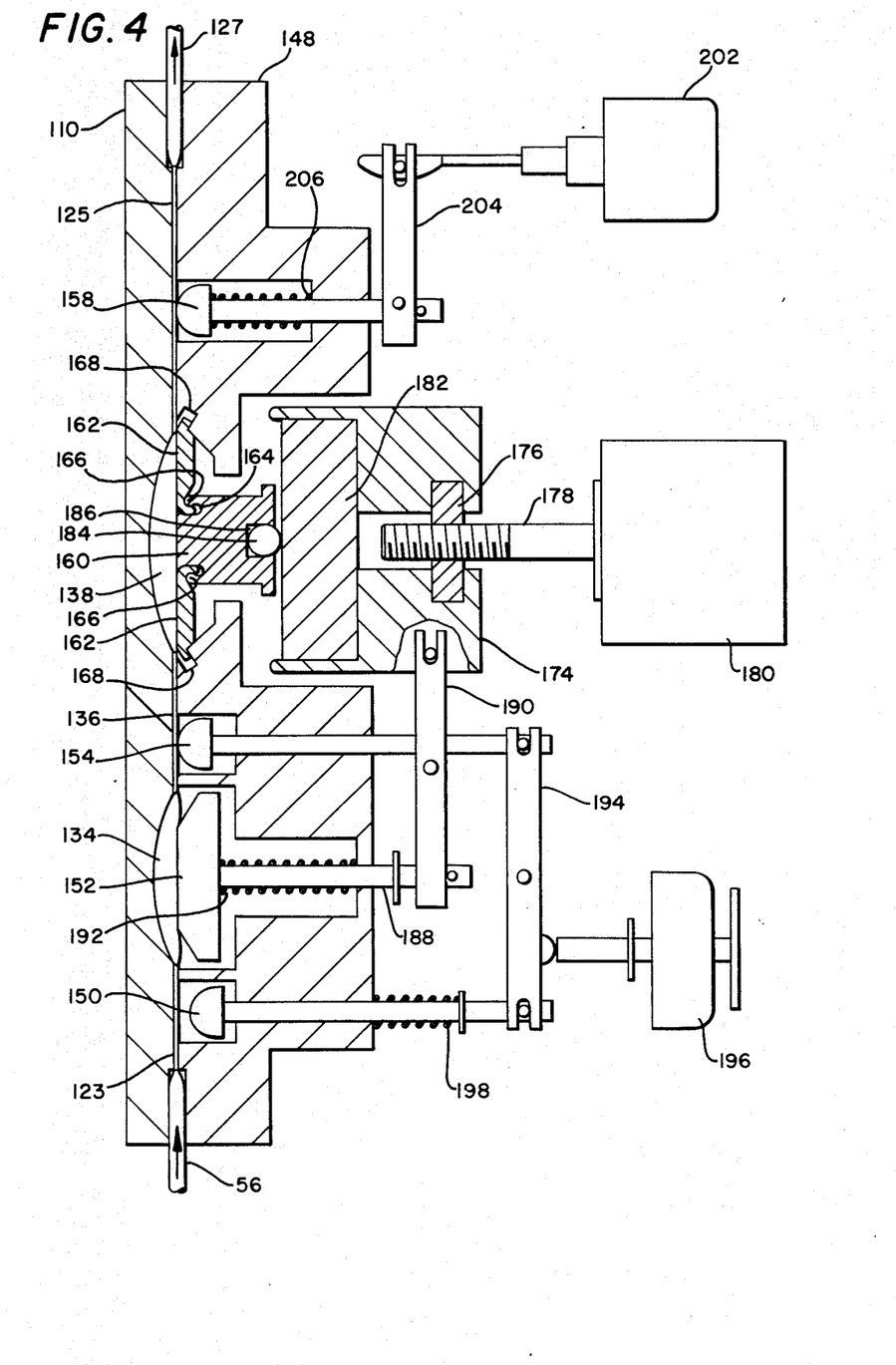
FIG. 4 is a cross-sectional view of the infusion pump of FIG. 1.
Figure 5:
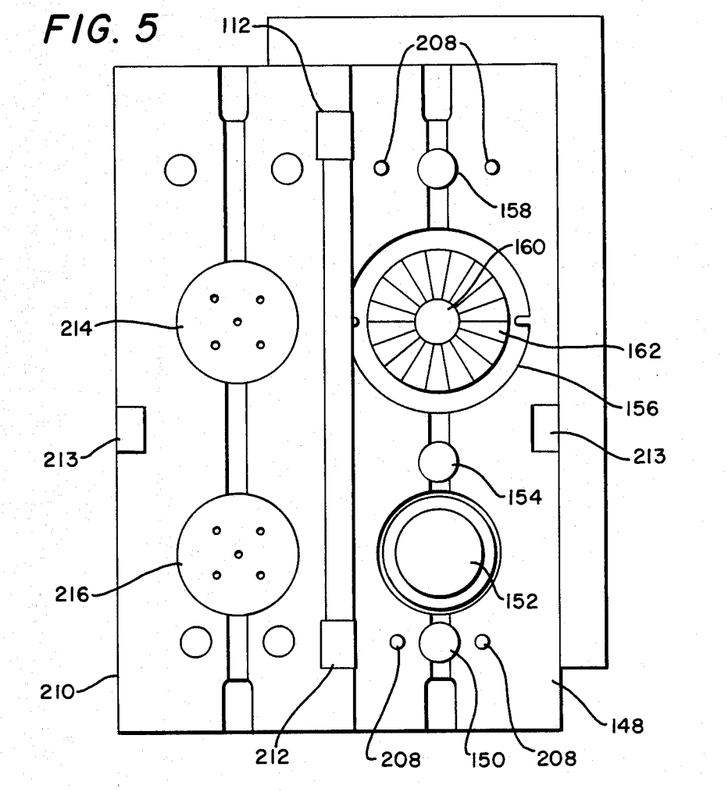
FIG. 5 is a front view of the pump prior to mounting the disposable cassette.

The moving members which operate upon cassette 122 when it is in operating position are arrayed on panel 148 secured of pump 26 as shown in FIGS. 4 and 5. Proceeding from upstream, the major elements are: inlet valve 150, refill pressure member 152, transfer valve 154, petal assembly pumping member 156, and delivery valve 158.

Figure 6:
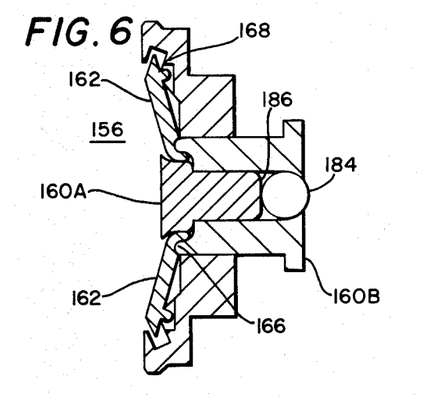
FIG. 6 is a partial cross-sectional view of the pumping member shown in the retracted position.
Figure 7:
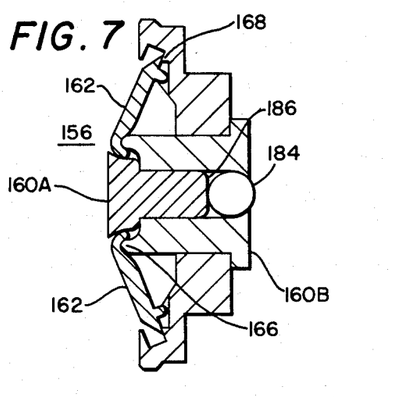
FIG. 7 is a partial cross-sectional view showing the pumping member of the infusion pump in the extended position.

Petal assembly 156 includes a central hub 160 surrounded by a plurality of petal shaped sections 162 to form the movable pressing surface which produces pumping pressure in the device. As best shown in FIGS. 6 and 7, the hub 160 is formed by press fit of male hub member 160A, and female hub member 160B. A circular recess 164 near the outer edge of hub 160 is formed between the two hub members. Each petal section 20 162 is provided on the rear face of its inner end with a smooth hooked-shape curve portion 166 which corresponds to a smooth curve provided on the hub recess 164. The inner end of each petal section 162 is pivotally retained in the hub recess 164, with the complimentary smooth curves of each member 25 permitting relative pivotal movement of each petal shaped section with respect to the hub about an axis adjacent recess 164. The instrument body panel 148 is provided with an annular petal nest 168 that circumferentially surrounds hub 160 and retains the outer end of each petal shaped section 30 162. The confronting surfaces of petal nest recess 168 and the outer end of each petal shaped section 162 are also shaped for smooth pivoting of the petal shaped sections with respect to the instrument body about an axis adjacent the nest 168.

A movable carriage 174 is mounted behind hub 160, and carries a drive nut 176 which is engaged with the threads of a threaded motor shaft 178 rotated by stepper motor 180. The forward end of carriage 174 is recessed to receive a load cell 182. Load cell 182 has its central force-measuring diaphragm confronting a metal ball 184 retained in a rear central recess 186 formed on hub 160. Thus, rotation of stepper motor 180 acts through the cooperation of threaded motor shaft 178 and carriage nut 176 to drive carriage 174 forward. This action transmits force through load cell 182 and metal ball 184 to hub 160, moving the hub forward. The translational motion of hub 160 also causes each petal shaped section 162 to pivot near each of its ends. The petal assembly thus forms a truncated cone of varying height as the hub moves between the extreme positions illustrated in FIGS. 6 and 7.

Refill pressure member 152 is carried at the forward end of refill shaft 188, which is driven either forwardly or rearwardly through lever 190 acted upon by the carriage 174. Thus, as viewed in FIG. 4, when carriage 174 is moving forwardly to push the petal assembly forward, the action of refill lever 190 causes shaft 188 and refill pressure member 152 to be withdrawn. As motor 180 is driven in the opposite direction to withdraw carriage 174, lever 190 allows the refill pressure member 152 to move forward. Spring 192 biases refill pressure member 152 to its forward position, and thus carriage 174 to the rearward direction.

Inlet valve 150 and transfer valve 154 have rounded surfaces for engaging the flow path of the cassette, and are operated in tandem fashion through inlet valve lever 194 driven by solenoid 196. When one of the two valves is in the open or rearward position, the other is necessarily in the closed or forward position. Bias to inlet valve lever 194 is provided by spring 198 surrounding the inlet valve shaft, which biases the arrangement to the condition of inlet valve open, transfer valve closed.

Delivery valve 158 is operated by a linear stepper motor 202 acting through delivery valve lever 204, and is biased to the closed position by spring 206. The linear stepper motor 202 is capable of positioning the delivery valve 158 in any position from fully retracted or open position, as shown, to a fully extended or closed position.

Actuator panel 148 is provided with mounting pins 208 corresponding to the mounting holes 142 in cassette 12. Inner door 210 is mounted to panel 148 by hinges 212 and is closed by latch 213. In the inner face of door 210, concave depression 214 is arranged to confront petal assembly 156 when the door is closed, and similar concave depression 216 confronts the refill pressure member 152. Depressions 214 and 216 are provided with air vent holes through the front of the door to facilitate closing of the door with the cassette 122 in position. With the cassette mounted on pins 208, the pump chamber 138 of the cassette is captured between petal assembly 156 and door depression 214. The supply chamber 134 is likewise captured between pressure member 152 and door depression 216. In the operating position, valve 158 is adjacent inlet passage 123 to close off the inlet when valve member 150 is extended. Likewise, valve 154 may be activated to close off transfer passage 136. The delivery valve 158 may be activated to selectively close outlet 125 of cassette 122, to an orifice of any desired size. The pumping compartment defined between the rigid wall of depression 214 and the petal assembly 156 must be completely filled by the fluid filled pump chamber 138 when the petal assembly 156 is in its retracted position illustrated in FIG. 6, and the pump chamber 138 is bulged with fluid at the low fluid pressure of approximately 10 inches of water. The volumetricity of pumping is then provided by the accuracy of volume displaced between the extreme positions of the petal assembly 156 illustrated in FIGS. 6 and 7, and the compliance of sheet 128 to the moving truncated cone surface presented by the petal assembly 156.

Since the material used to construct the cassette is flexible it conforms to the surface of the petal elements so that the position of the petal assembly defines the volume of fluid enclosed between it and the spherical surface on the other side very precisely. This enables the volumetric performance of this arrangement to be defined almost completely by the movement of the hub, and thus of the petal shaped sections, and not by the mechanical properties of the disposable element. The volume displaced by the petal assembly varies in a linear fashion with the translational movement of hub 60.

Figure 11:
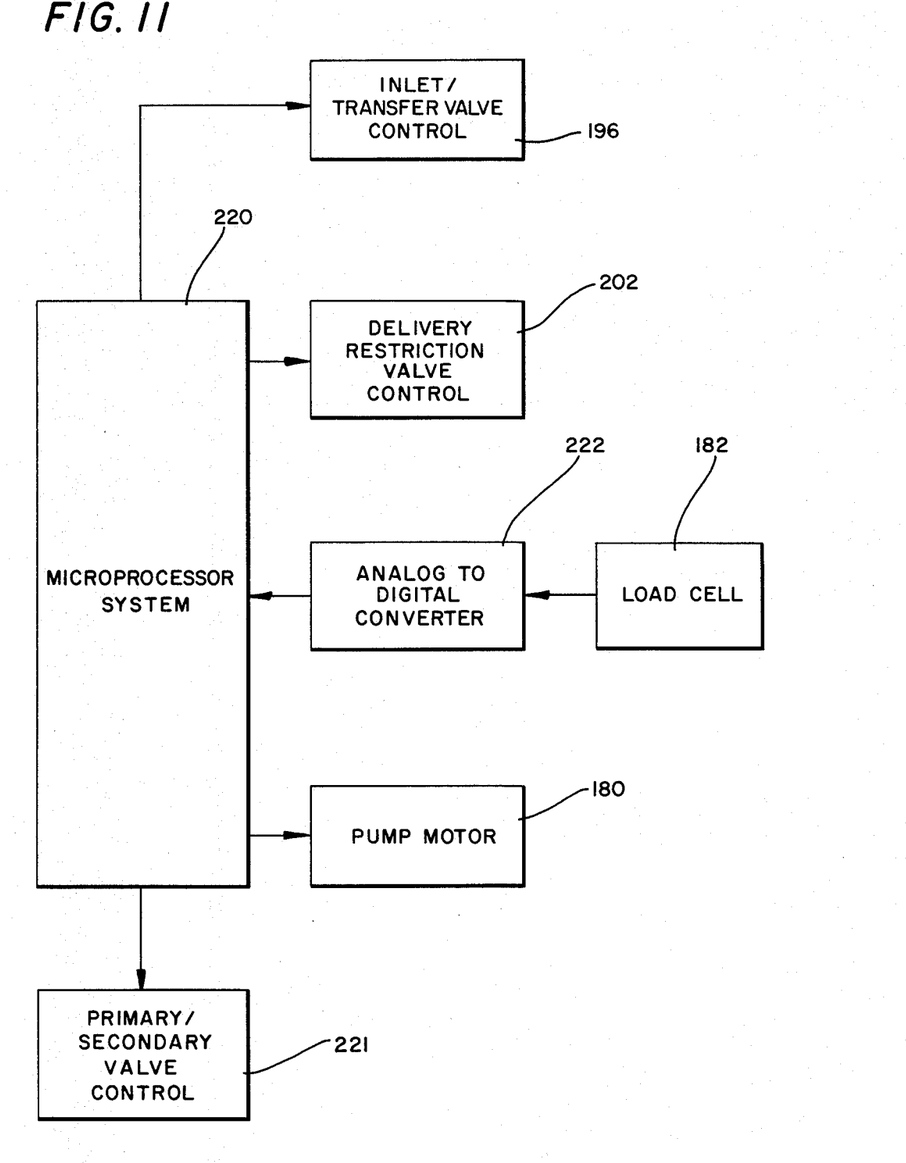
FIG. 11 is a schematic of the electronic controls within the infusion pump.

As illustrated in FIG. 11, the pump is operated under the control of a microprocessor system 220. The microprocessor, as illustrated in FIG. 11, controls the movement of solenoid 196 between its two positions: (1) inlet valve open, transfer valve closed, and (2) inlet valve closed, transfer valve open. Likewise, microprocessor 220 controls delivery valve stepper motor 202 to select the total or partial restriction imposed by delivery valve 158 on the cassette outlet 125. Microprocessor 220 also selects, in accordance with the rates selected by the operator, the rate of movement of the pumping stepper motor 180. Microprocessor 220 also governs the primary/secondary valve control 221. Continuous control over operation, and diagnostics for abberant conditions, are principally provided by load cell 182 which directly measures the force being exerted on the pump chamber 138 by petal assembly 156. This data is continuously provided to microprocessor 220 through A/D converter 222.

Figure 8:
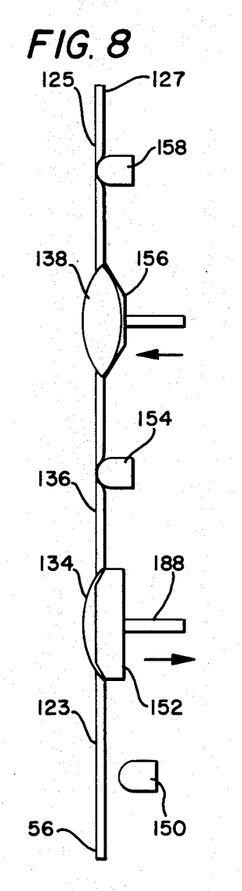
FIGS. 8, 9 and 10 illustrate schematically the operational sequence of the infusion pump.
Figure 9:
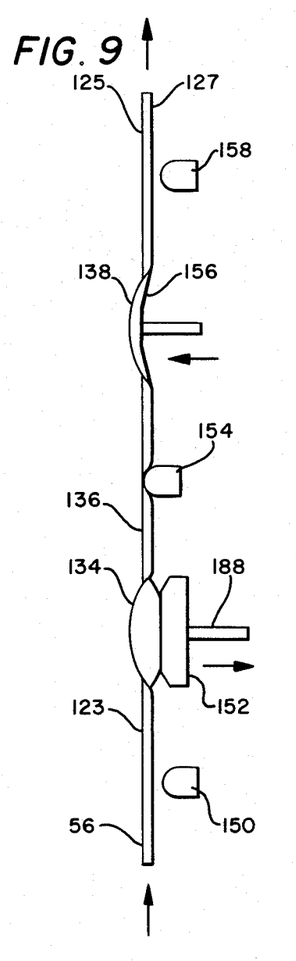
Figure 10:
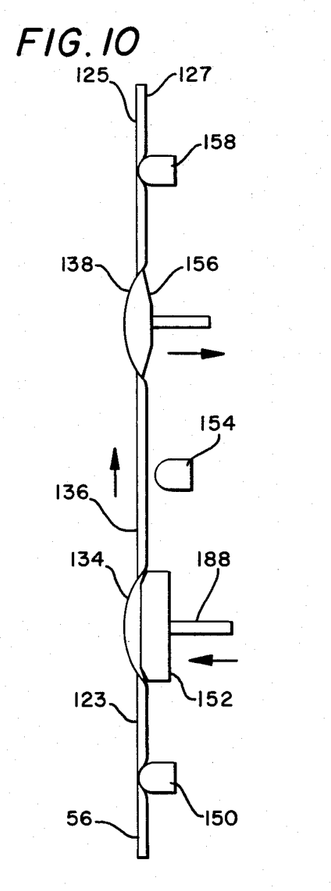

A typical cycle of pumping operation is illustrated in FIGS. 8 through 10. FIG. 8 illustrates the condition of the pump and disposable as the delivery portion of the cycle has begun. At this stage, the pump chamber 138 has been completely filled with fluid to occupy the compartment with petal assembly 156 fully retracted. Delivery valve 158 and transfer valve 154 are closed, completely capturing the fluid in pump chamber 138. Inlet valve 135 is opened, so that fluid may enter the supply chamber 134 by gravity as refill pressure member 152 is retracted. In this initial stage, the microprocessor begins the initial stage of the delivery cycle by directing the pump chamber stepper motor 180 to advance to begin pressurization of the fluid in pump chamber 138. During the first few steps of operation, valves 158 and 154 remain closed to permit this initial pressurization. Elevation of the force required to advance the petal assembly 156 is sensed by load cell 182 which data is fed to the microprocessor 220. This state serves as a diagnostic to verify the capturing of a full load of fluid in the pump chamber 138. A failure to pressurize in the first several steps of motor 180 indicates a lack of secondary fluid entering supply chamber 134. Accordingly, primary/secondary valve control 221 is directed to close the secondary valve and open the primary valve, and the rate is changed by microprocessor 220 to the selected primary rate. If some other fault continues to cause a lack of pressurization in the chamber 138, operation of the instrument will be stopped by the microprocessor 120 and an alarm sounded.

If however, normal pressurization occurs, microprocessor 120 instructs delivery valve 158 to open as motor 180 advances, to deliver fluid to the patient through outlet 125, as illustrated in FIG. 9. Continuous monitoring of load cell 182 permits the microprocessor to exercise continuous control over delivery valve 158 to selectively restrict the outlet 125. This permits the device to ensure that gravity siphoning at a higher rate than the requested rate does not occur. The microprocessor is also programmed with a selected maximum pressure limit set by the user which is used in the continuous pressure monitoring. Escalation of pressure above the selected maximum pressure, even with the delivery valve 158 wide open, will result in alarm and shutdown of the instrument, indicating that there is some occlusion which requires nursing attention, and that fluid is not reaching the patient. The ability to select maximum pressure limit by the user permits relatively rapid occlusion alarms, even at relatively low selected infusion rates.

Preferably, the microprocessor is programmed to maintain a relatively constant pressure in pump chamber 138 by selective restriction of delivery valve 158, such constant pressure being just below the maximum pumping pressure selected by the operator. This is helpful in ensuring that there are no variations in volumetric delivery which might result from operation at varying pumping pressures.

While fluid is being delivered by advancement of the petal assembly 156, the refill pressure member 152 is automatically being withdrawn, and fluid is entering the supply chamber 134 by gravity through open inlet 123. When petal assembly 156 has reached its fully extended position, illustrated in FIG. 7, valves 150 and 158 close, and valve 154 opens. Microprocessor 220 then reverses stepper motor 180 for a rapid retraction of petal assembly 156 and a rapid extension of refill pressure member 152 as illustrated in FIG. 10. This permits a very quick transfer of fluid into pump chamber 138 which will arm the device for the next delivery cycle. During the pumping portion of the delivery cycle energy was stored in the spring 192 immediately behind the refill pressure member 152. This energy is used to effect the transfer of fluid so as to drastically reduce the mechanical loading on the main pump motor. The purpose of this is to allow an increased motor speed during the fluid transfer step which in turn reduces the time taken to effect the transfer as it is principally limited only by the maximum operating speed of the main pump motor 180. Once the transfer of fluid is complete, valve 150 opens and valve 154 closes and the system is in the condition once more indicated in FIG. 8. A mechanical stop on shaft 188 limits the amount of movement of the refill piston 152 so as to avoid pumping any fluid back towards the fluid container 20 as valve 150 opens.

It will be appreciated that the cassette and instrument could be designed without supply chamber 134, refill pressure member 152, and transfer valve 154, but in that event the refill cycle time would be dependent upon the rate of flow into pump chamber 138 dictated by natural forces of gravity. Use of the device in the form illustrated permits the instrument to control the time taken up by the refilling of pump chamber 138, and to cause that step to happen rapidly to limit the duration of the refilling cycle.

The changeover from secondary fluid delivery at the selected secondary rate to primary fluid delivery at the selected primary rate occurs automatically, because of pressure detection in the pump chamber 138. Because the Y-connector is located at or just below the level of supply chamber 134, secondary fluid will cease to gravity fill the supply chamber 134 before its fluid column falls to connector 54. This results in shiftover when the secondary fluid is depleted just above connector 54.

Although specific embodiments of the inventions have been illustrated in the accompanying drawings and described in the foregoing detailed description, it will be understood that the invention is not limited to the embodiments disclosed, but is capable of numerous rearrangements, modifications and substitutions of parts and elements without departing from the spirit of the invention.

We claim:

1. A system for administering to a patient fluid from a secondary fluid container at a selected secondary flow rate, followed by fluid from a primary fluid container at a selected primary flow rate, in which the rates are governed at a rate control site by an electromechanical device, the system comprising:
   a Y-connector upstream from the rate control site;
   a primary fluid tube extending from the primary fluid container to the Y-connector through a primary valve; a secondary fluid tube extending from the secondary fluid container to the Y-connector through a secondary valve;
   an output flow tube extending from the Y-connector toward the patient whereby a primary fluid path is provided from the primary container to the device through the primary fluid tube, Y-connector and output flow tube, and a secondary fluid path is provided from the secondary container to the device through the secondary fluid tube, Y-connector and output flow tube;
   detection means for automatically detecting the absence of fluid at a location in the secondary fluid path near the Y-connector, said location being selected so that no fluid holding means other than tubing is interposed in the secondary fluid path below the detection means and above the Y-connector; and
   switching means responsive to detection by the detection means to close the secondary valve and open the primary valve, and thereafter cause the device to govern flow at the rate selected for the primary fluid.

2. The system of claim 1 wherein the rate control site includes a chamber in the output tube filled from the supply containers by gravity, the Y-connector is secured no higher than the approximate height of the chamber, and the detection means includes means for detecting the lack of fluid filling the chamber.

3. The system of claim 1, wherein the detection means comprises an air-in-line detector positioned on the secondary fluid tube near the Y-connector.

4. The system of claim 1, including input means for the user to input a volume to be delivered at the secondary rate, and wherein said switching means responsive to the detection means is also responsive to completion of delivery of the selected volume at the secondary rate so that, if the delivery of such selected volume occurs prior to detection of absence of fluid in the secondary line, said switching means will be activated.

5. A device for administering to a patient fluid from an elevated secondary fluid container at a selected secondary flow rate, followed by fluid from an elevated primary fluid container at a selected primary flow rate, comprising:
   an instrument body having a movable pumping actuator;
   a pump cassette removably mounted in the instrument body, having an inlet for receiving fluid from the containers by gravity fill and an outlet for delivering fluid under the influence of the pumping actuator, and having a pumping chamber between the inlet and outlet adjacent the pumping actuator;
   a delivery tube extending from the cassette outlet to the patient;
   a supply tube extending from the cassette inlet toward the fluid containers;
   a primary fluid tube extending from the primary fluid container toward the instrument body;
   a secondary fluid tube extending from the secondary fluid container toward the instrument body;
   a Y-connector joining the primary fluid tube, secondary fluid tube and supply tube, located at the approximate level of the cassette at a height which will not permit a fluid head just upstream from the connector to fill the cassette by gravity;
   a primary fluid valve located on the primary fluid tube adjacent the connector;
   a secondary fluid valve located on the secondary fluid tube adjacent the connector;
   detection means for detecting a lack of fluid filling the cassette, including means for sensing a lack of pressure elevation as the pumping actuator is moved against the pumping chamber;
   means responsive to said detection means for closing the secondary valve and opening the primary valve; and means for controlling the pumping actuator at a first selected rate of fluid delivery when the secondary valve is open and the primary valve is closed, and at a second selected rate of fluid delivery when the secondary valve is closed and the primary valve is open.

6. A system for administering to a patient fluid from a secondary fluid container at a selected secondary flow rate, followed by fluid from a primary fluid container at a selected primary flow rate, in which the rates are governed at a rate control site by an electromechanical device, the system comprising:
- a Y-connector upstream from the rate control site;
- a primary fluid tube extending from the primary fluid container to the Y-connector through a primary valve;
- a secondary fluid tube extending from the secondary fluid container to the Y-connector through a secondary valve;
- an output flow tube extending from the Y-connector toward the patient whereby a primary fluid path is provided from the primary container to the device through the primary fluid tube, Y-connecter and output flow tube, and a secondary fluid path is provided from the secondary container to the device through the secondary fluid tube, Y-connector and output flow tube;
- air-in-line detection means positioned on the tubing of the secondary fluid path for automatically detecting the absence of fluid in the tubing of the secondary fluid path at a location in the secondary fluid path adjacent the Y-connector; and
- switching means responsive to detection by the air-in-line detection means to close the secondary valve and open the primary valve, and thereafter cause the device to govern flow at the rate selected for the primary fluid.

* * * * *